United States Patent
Eakins et al.

(10) Patent No.: US 9,078,995 B2
(45) Date of Patent: Jul. 14, 2015

(54) IRIS RETRACTION BALLOON FOR PHACOEMULSIFICATION

(75) Inventors: Matthew Eakins, Chicago, IL (US); Christopher Eakins, Chicago, IL (US); Thomas Eakins, Spring Park, MN (US)

(73) Assignee: XYGENT VISION CARE INSIGHT, Eden Prairie, MN (US)

( * ) Notice: Subject to any disclaimer, the term of this patent is extended or adjusted under 35 U.S.C. 154(b) by 171 days.

(21) Appl. No.: 13/099,690

(22) Filed: May 3, 2011

(65) Prior Publication Data
US 2012/0059404 A1    Mar. 8, 2012

Related U.S. Application Data

(60) Provisional application No. 61/334,274, filed on May 13, 2010.

(51) Int. Cl.
- *A61M 29/02* (2006.01)
- *A61B 17/02* (2006.01)
- *A61B 17/00* (2006.01)
- *A61F 9/007* (2006.01)

(52) U.S. Cl.
CPC ............ *A61M 29/02* (2013.01); *A61B 17/0231* (2013.01); *A61B 2017/00557* (2013.01); *A61F 9/00736* (2013.01)

(58) Field of Classification Search
CPC ........... A61B 17/3423; A61B 17/0231; A61B 17/0293; A61F 2/1694; A61M 29/02
USPC .......... 606/107, 192, 198; 600/207, 208, 236; 623/6.12
See application file for complete search history.

(56) References Cited

U.S. PATENT DOCUMENTS

| | | | |
|---|---|---|---|
| 3,991,426 A | 11/1976 | Flom et al. | |
| 5,171,266 A | 12/1992 | Wiley et al. | |
| 5,299,564 A * | 4/1994 | Sabatino | 600/236 |
| 5,476,512 A * | 12/1995 | Sarfarazi | 623/6.39 |
| 5,628,795 A | 5/1997 | Langerman | |
| 5,697,973 A | 12/1997 | Payman et al. | |
| 6,620,098 B1 * | 9/2003 | Milverton | 600/236 |
| 2006/0047339 A1 * | 3/2006 | Brown | 623/6.13 |
| 2008/0269888 A1 | 10/2008 | Malyugin | |

OTHER PUBLICATIONS

International Search Report and Written Opinion from related PCT Application PCT/US2011/035100, dated Jan. 18, 2012, 10 pages.
International Preliminary Report on Patentability from related PCT Application PCT/US2011/035100, dated Nov. 22, 2012, 3 pages.

* cited by examiner

*Primary Examiner* — Thomas McEvoy
(74) *Attorney, Agent, or Firm* — Norton Rose Fulbright US LLP; Scott D. Rothenberger

(57) ABSTRACT

Provided is an inflatable ring device useful for expanding the iris prior to ophthalmic surgery. The ring shape is either continuous or discontinuous and includes a groove around the outer periphery of the ring. When inflated, the groove engages the inner periphery of the iris and continued inflation thereby expands the iris to a desired size allowing increased access to the eye. The invention also provides a method of expanding the iris prior to performing ophthalmic surgery comprising placing an inflatable ring shaped device in the anterior chamber of the eye. Inflating the inflatable ring shaped device until a groove around the outer periphery of the ring shaped device engages the iris and continued inflation of the ring shaped device continues to expand the iris to a desired size.

15 Claims, 1 Drawing Sheet

IRIS RETRACTION BALLOON FOR PHACOEMULSIFICATION

CROSS REFERENCE TO RELATED APPLICATION(S)

This application claims benefit under 35 U.S.C. §119(e) to U.S. Provisional Patent Application No. 61/334,274, filed May 13, 2010, entitled "IRIS RETRACTION BALLOON FOR PHACOEMULSIFICATION", the contents of which is incorporated herein in their entirety for all purposes.

FIELD OF THE INVENTION

The invention is directed to an inflatable expansion ring for the iris for use during an ophthalmic surgical procedure.

BACKGROUND OF THE INVENTION

Various ophthalmic surgical procedures require prolonged and/or exact dilation of the iris. Such procedures include phacoemulsification, which is the process of removing the lens due to cataracts or glaucoma. In such procedures, the iris must be held at an optimum dilation in order to insert surgical instruments into the eye through the pupil. In many cases, it is sufficient to provide a mydriatic, such as tropicamide into the eye to achieve sufficient pupil dilation. In some instances, either because the eye is too small, the pupil is too small, the eye is simply incapable of dilating sufficiently or because of the presence of complication from other medications, such as floppy iris syndrome, various mechanical devices have been fabricated to maintain a correct retraction of the iris.

Currently, there are a number of devices designed for expanding or dilating the iris during surgery. These devices include iris hooks, expansion rings, partial rings and instruments which include fixed tension rings on the end. However, all of these devices are limited by their ease, or lack thereof, of insertion and removal. For example, iris hooks require a separate incision through the cornea for each hook and an individual attachment of the iris for each hook. Thus, as at least four hooks are needed to retract the iris during a procedure, and the risk of damage to the eye is concomitantly increased.

Expansion rings require only a single incision for insertion, however, the main disadvantages of such technologies include their bulkiness and rigidity, making them difficult to insert, remove, and manipulate inside the iris through a small incision. Expansion rings are designed to fit inside the pupil and support the iris in an open position. However, they function because they ultimately provide a rigid or semi-rigid device which, in effect, "props" the iris open during surgery. Unfortunately, the need to provide a rigid or semi-rigid bulwark inside the eye makes the insertion and removal of such devices potentially harmful to the eye. Further, such devices are difficult to position if the anterior chamber is shallow or the pupil is less than 4 mm wide. Thus, various size rings are used depending on the size of the patient's eye. However, in some cases, a small size ring is first inserted only to have the iris continue to dilate or to be affected by "Floppy Iris Syndrome" and the ring becomes useless requiring removal before or during surgery. This, too, can result in damage to the eye.

For example, published U.S. patent application 2008/0269888 to Malyugin, discloses a spring-like device contained within an applicator. When deployed, the applicator is inserted through an incision in the cornea and the ring is ejected into the anterior chamber of the eye. Upon ejection, the ring springs open to resemble a square or rectangular wire frame with loops at each corner. In use, a portion of the rim of the patient's iris is inserted into the loops to be clasped thereby. Due to its latent energy, the act of deploying the ring in the eye provides some risk. Further, the use of spring loops to grasp discrete sections of the iris provides opportunities to tear or damage the iris both during insertion and during removal. In addition, even after the portions of iris tissue have been removed from the grasp of the spring loops, the Malyugin ring (now in its extended form) must be removed from the eye using the same small incision. This process sometimes results in the ring being simply cut into pieces to afford its more convenient removal providing further risks due to smaller debris now taking its place.

Similarly, U.S. Pat. No. 6,620,098 to Milverton describes a device for dilating a pupil comprising a discontinuous ring that is deformable so as to be ejected from a catheter or other injection device in a linear form but then re-form its circular shape once deployed in the anterior chamber. The device described by Milverton also has scalloped flange portions on either side of a connecting body portion, the combination defining a space in which the iris is positioned. When deployed, the surgeon extrudes the device into the anterior chamber and then threads the device around the iris which is held in place by the opposing scallops. Those of skill in the art appreciate that the ability to securely hold the iris in the desired position with the device of Milverton is a function of the passive recoil of the device versus the tension of the iris. If the iris is small and the tension is large, the device may not have the recoil to provide proper dilation. If the iris is too big or the patient suffers from floppy iris syndrome, the device will not be able to maintain contact with the iris and the device will be useless.

Due to the difficulty of insertion, difficulty of retraction and risk of damage to the eye of current devices for iris expansion, it would be beneficial to provide an iris expansion device that is easier to insert, does not require latent kinetic energy to insert and is able to expand to multiple sizes without having to use different size expansion rings.

SUMMARY OF THE INVENTION

Provided is an inflatable ring device useful for expanding the iris prior to ophthalmic surgery. The ring shape is either continuous or discontinuous and includes a groove around the outer periphery of the ring. When inflated, the groove engages the inner periphery of the iris and continued inflation of the ring expands the iris to the desired size allowing increased access to the eye. The invention also provides a method of expanding the iris prior to performing ophthalmic surgery comprising placing an inflatable ring shaped device in the anterior chamber of the eye. Inflating the inflatable ring shaped device until a groove around the outer periphery of the ring shaped device engages the iris and continued inflation of the ring shaped device continues to expand the iris to a desired size. The invention can be used for clinical and veterinary purposes.

The present invention provides an inflatable iris expansion ring that is easier to deploy and remove than current iris expansion devices and, further, does not require different sizes depending on the size of the iris.

Therefore, in various exemplary embodiments, the invention includes an inflatable ring device for deployment in the eye such that when the device is inflated, a groove is provided in the outer periphery of the inflatable ring, the groove then engages the iris, increasing the diameter of the pupil.

In some exemplary embodiments, according to the invention, the inflatable ring is discontinuous having approximately a horseshoe shape. In various exemplary embodiments, the grove is approximately 'V' or 'U' shaped.

In various exemplary embodiments, the device is fabricated from a biocompatible material such as rubber, plastic or nylon or combinations thereof. In some exemplary embodiments, the device is fabricated from polymers or copolymers such as polyamides or polyamides and polyether. In other exemplary embodiments, the inflatable expansion device is fabricated from polymers such as polypropylene, polyethylene terephthalate or other phthalate polyesters or copolyesters, and nylons.

In use, the device can be inflated by filling it with air such as through a syringe attached to the valve or inserted through the resealable portion. In other embodiments, the device inflates passively such as when it is filled with a hypertonic solution. In other embodiments, the device can be made with recoil such that the device is packaged deflated and sealed. When deployed, the device expands, thereby drawing air into the device and inflating. In this aspect, the check valve, thermal expansion valve, pinch valve or the like is then usable to maintain the inflation of the device while in use.

In still other exemplary embodiments, the device includes one or more positioning loops. In these embodiments, the positioning loops are spaced around the periphery of the device allowing manipulation of the device using a forceps or hook. In some exemplary embodiments, the positioning loops further include holes or eyelets therein to allow for a hook (such as a Kuglen) to grasp the loop.

In still other exemplary embodiments, the invention provides a method of expanding an iris such as is suitable for allowing ophthalmic surgery. The method including: deploying an inflatable ring device in the anterior chamber of an eye; inflating the inflatable ring device; engaging a groove on the outer periphery of the inflatable ring device with the inner periphery of the iris; and expanding the inflatable ring device as needed to allow access to the eye.

In some exemplary embodiments according to the invention, the method also includes engaging the iris by positioning the inflatable ring device using a positioning loop attached to the inflatable ring device.

In still other exemplary embodiments, the step of inflating is performed by injecting air from a syringe into an air-inlet valve located on the inflatable ring device. However, in various other exemplary embodiments, the step of inflating is accomplished by allowing the device to inflate such as in response to an elastic recoil or in response to normal saline irrigation once the device is deployed.

These and other features and advantages of the present invention will be set forth or will become more fully apparent in the description that follows and in the appended claims. The features and advantages may be realized and obtained by means of the instruments and combinations particularly pointed out in the appended claims. Furthermore, the features and advantages of the invention may be learned by the practice of the invention or will be apparent from the description, as set forth hereinafter.

BRIEF DESCRIPTION OF THE FIGURES

Various exemplary embodiments of the compositions and methods according to the invention will be described in detail, with reference to the following figures wherein.

DETAILED DESCRIPTION OF THE EXEMPLARY EMBODIMENTS

Figure 1A:
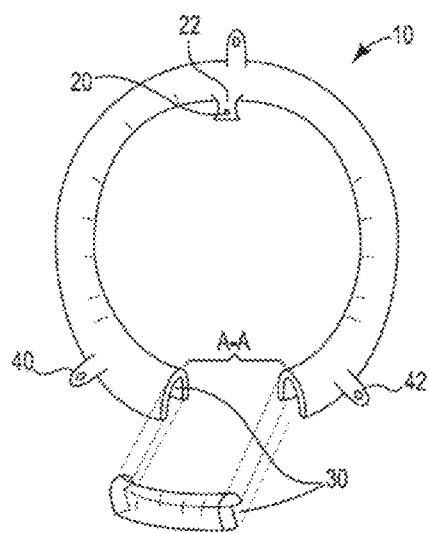
FIGS. 1A and 1B illustrate two exemplary embodiment of an iris expansion device according to the invention. In the exemplary embodiment illustrated in FIG. 1A, the iris expansion device is ring-shaped. In this exploded diagram, the interior of the donut shaped iris expansion device is visible with piece 'b' removed along lines A-A. In the exemplary embodiment illustrated in FIG. 1B, the iris expansion device is a discontinuous ring or roughly horseshoe shaped ring.

Provided is an inflatable ring device useful for expanding the iris prior to ophthalmic surgery. The ring shape is either continuous or discontinuous and includes a groove around the outer periphery of the ring. When inflated, the groove engages the inner periphery of the iris and continued inflation of the ring expands the iris to the desired size allowing increased access to the eye. The invention also provides a method of expanding the iris prior to performing ophthalmic surgery comprising placing an inflatable ring shaped device in the anterior chamber of the eye. Inflating the inflatable ring shaped device until a groove around the outer periphery of the ring shaped device engages the iris and continued inflation of the ring shaped device continues to expand the iris to a desired size. The invention can be used for clinical and veterinary purposes.

The present invention provides an inflatable iris expansion ring that is easier to deploy and remove than current iris expansion devices and, further, does not require different sizes depending on the size of the iris.

Therefore, in various exemplary embodiments, the invention includes an inflatable ring device for deployment in the eye including a groove provided in the outer periphery of the inflatable ring. When the device is inflated, the groove engages the iris, as inflation increases the diameter of the ring increases, increasing the diameter of the pupil.

In some exemplary embodiments, according to the invention, the inflatable ring is discontinuous having approximately a horseshoe shape. In various exemplary embodiments, the groove is approximately 'V' or 'U' shaped.

In various exemplary embodiments, the device is fabricated from a biocompatible material such as rubber, plastic or nylon or combinations thereof. In some exemplary embodiments, the device is fabricated from polymers or copolymers such as polyamides or polyamides and polyether. In other exemplary embodiments, the inflatable expansion device is fabricated from polymers such as polypropylene, polyethylene terephthalate or other phthalate polyesters or copolyesters, and nylons.

In use, the device can be inflated by filling it with air such as through a syringe attached to the valve or inserted through the resealable portion. In other embodiments, the device inflates passively such as when it is filled with a hypertonic solution. In other embodiments, the device can be made with recoil such that the device is packaged deflated and sealed. When deployed, the nipple or valve is unsealed, the device expands, thereby drawing air into the device and inflating. In this aspect, the check valve, thermal expansion valve, pinch valve or the like is then usable to maintain the inflation of the device while in use.

In still other exemplary embodiments, the device includes one or more positioning loops. In these embodiments, the positioning loops are spaced around the periphery of the device allowing manipulation of the device using a forceps or hook. In some exemplary embodiments, the positioning loops further include holes or eyelets therein to allow for a hook (such as a Kuglen) to grasp the loop.

In still other exemplary embodiments, the invention provides a method of expanding an iris such as is suitable for allowing ophthalmic surgery. The method including: deploying an inflatable ring device in the anterior chamber of an eye; inflating the inflatable ring device; engaging a groove on the outer periphery of the inflatable ring device with the inner periphery of the iris; and expanding the inflatable ring device as needed to allow access to the eye.

In some exemplary embodiments according to the invention, the method also includes engaging the iris by positioning the inflatable ring device using a positioning loop attached to the inflatable ring device.

In still other exemplary embodiments, the step of inflating is performed by injecting air from a syringe into an air-inlet valve located on the inflatable ring device. However, in various other exemplary embodiments, the step of inflating is accomplished by allowing the device to inflate such as in response to an elastic recoil or in response to normal saline irrigation once the device is deployed.

In still other exemplary embodiments, the step of inflating is performed by injecting air from a syringe into an air-inlet valve located on the inflatable ring device. Alternatively, in other embodiments, the device is inflated by creating an osmotic gradient resulting in water in-flow into the device or by an elastic recoil of the deflated device when deployed.

Figure 1B:
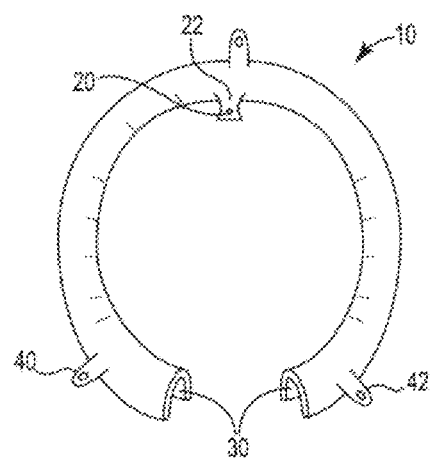

Referring now to FIGS. 1A and 1B, two exemplary embodiments of the iris expansion device 10, according to the invention, are illustrated. As shown in FIGS. 1A and 1B, the inflatable iris expansion device comprises a ring-shape or discontinuous ring shape. FIG. 1A shows one embodiment of the instant invention where the ring shaped device comprises a complete ring. An air inlet valve 20 is positioned at a convenient place on the ring 10. In this illustration, a portion 'b' of the ring is removed along line A-A to illustrate the groove 30 running along the periphery of the ring 10. Also illustrated are positioning loops 40 placed roughly equidistantly around the periphery of the ring. In some embodiments, the positioning loops also have eyelets 42 so that a hook, such as a Kuglen hook or other instrument, can be inserted into the eyelet to aid in positioning the device.

In some exemplary embodiments, the iris expansion device is contained within an applicator. Those of skill in the art will appreciate that any applicator suitable for insertion of the applicator through the incision can be used. However, in some exemplary embodiments, the applicator is a syringe or other pipet-type device.

In use, the applicator is inserted through an incision made in the cornea of the eye. The ring-shaped device is deployed into the anterior chamber of the eye by ejecting it from the applicator. Once in the anterior chamber, the device can be positioned using a hook, such as a Kuglen hook, engaged to one of the eyelets 42 is a positioning loop 40 located on the device 10. The device can then be inflated by attaching a syringe or other means of inflation to an air inlet valve. In some exemplary embodiments, the valve 20 is on a stem 22. Further, the valve can be either a one-way valve or a two-way valve. The air inlet valve can be any suitable valve such as, for example, a Luer lock, a screw, a self-sealing polymer, a check valve, osmotic valve, electromagnetic valve, pinch valve, thermal expansion valve or the like. Those of skill in the art will appreciate that when a two-way valve is used, following completion of a procedure, the air can be removed from the ring shaped device in an opposing manner from which it is injected. However, those of skill in the art can appreciate that a one-way valve can also be used to inflate the device and deflation can be achieved simply by puncturing the device such as by using, for example, a needle. In addition, if a self-sealing polymer is used, deflation of the device requires only insertion of a syringe into the inflated device and removal of the air using the syringe.

For example, in still other exemplary embodiments, the device includes an air-inlet valve. While the valve be any suitable valve, in some exemplary embodiments the valve comprises a Luer lock or a screw that is compatible with a syringe. In other exemplary embodiments, the valve is a self sealing polymer portion of the device. In other embodiments, the valve may be an electromagnetic valve, an osmotic valve, a check valve, a pinch valve, a thermal expansion valve or the like.

In other exemplary embodiments, the device is made of a self-sealing polymer such that a syringe can be inserted into the device and air is injected to inflate the device. When appropriate inflation is achieved, the syringe is withdrawn and the inflated device self-seals. In other exemplary embodiments, the device is shipped in an applicator and connected to an inflation device such that the device is ejected from the applicator into the eye and then inflated using the applicator. Further, those of skill in the art will appreciate that, while the entire device may be self-sealing, such that the syringe can be inserted into the device in any desirable place, in some embodiments, a nipple is provided on the device suitable for inflation and self-sealing after the syringe is withdrawn.

In other exemplary embodiments, the device may be manufactured with hypertonic saline solution sequestered inside. In this embodiment, the device may be implanted in the eye and when the eye is irrigated by a normal saline, the osmotic gradient of the hypertonic solution in the device would draw water into the device inflating it to an appropriate pressure predetermined by the gradient and the elastic recoil of the device.

In another exemplary embodiment, inflation of the device may be achieved by use of a check valve. In this embodiment, the one-way check valve is provided on a nipple or stem of the device allowing inflation using a syringe either with a needle or a screw-type adapter thereon allowing for the syringe to mate with the valve to inject air. To deflate the device, the syringe can simply be inserted therein and air withdrawn.

In another exemplary embodiment, the device includes a pinch-valve for inflation. In this embodiment, the device simply includes a port allowing for inflation. Sealing of the device is then achieved by a surgical staple or clip.

In a further exemplary embodiment, the device includes an electromagnetic valve. In this embodiment, the device uses a special injector that when engaged uses a current to magnetically open the valve changing the volume and/or pressure.

In another exemplary embodiment, the device includes a thermal expansion valve. In this embodiment, when the device reaches body temperature, expansion of the components seals the valve allowing the device to maintain inflation/pressure.

When deployed, the device is simply extruded from the applicator into the aqueous humor or the anterior chamber. The device is then positioned within the pupil or the opening of the iris. The device is then inflated so that it is approximately equal to the diameter of the pupil. Then, the device can be positioned manually, if necessary, using a surgical device or probe, such as a Kuglen hook, placed through one of the eyelets 42 of the positioning loops 40 located on the outside of the device 10. The device is positioned such that the groove 30 on the periphery of the device 10 engages the lip or inner periphery of the iris. Once the iris is engaged, the device can be inflated as much or as little as desired to achieve the optimum conditions for a surgeon. Those of skill in the art will appreciate that when using the instantly disclosed invention, only one size of device 10 is necessary as smaller pupils can accept the deflated device equally as well as larger pupils and consequent expansion of the iris is to any degree desired based on the degree of inflation.

Those of skill in the art will appreciate that while inflation can be accomplished by actively injecting air into the device, inflation can also be accomplished by creating an osmotic gradient sufficient to create a flow of water into the device when the eye is irrigated with normal saline following deployment of the device containing a hypertonic solution. Similarly, when the device is packaged in a collapsed state, the elastic recoil of the device unfolding in the eye can create enough pressure to inflate the device.

Those of skill in the art will appreciate that the benefits of the instant invention when compared to currently used devices used for iris expansion are many fold. First, the iris is contacted by the device around all or a majority of the periphery. This characteristic results in the force of expansion being distributed evenly around the iris and results in less chance for damage of the iris when the expansion pressure is applied to only one or several points of contact. In addition, because the device engages the iris by passively engaging the iris in the groove 30 as opposed to actively grasping the edge of the iris in a spring-type loop, there is less chance of tearing or damaging the iris due to incomplete detachment from the grasping device. Further, because the size of iris expansion is determined by the degree to which the device is inflated, only one-size of device is needed. This further increases the ease and safety of use of the device when the wrong size of expansion device is used due to increased dilation or "floppy" iris syndrome is a problem, due to the use of drugs such as flowmax. The design of the present invention allows the entire iris periphery to be supported by the device and, further, support can be maintained even when the iris continues to dilate or when the iris is "floppy" simply by inflating the device gently to continue support of the iris around its entire edge.

Those of skill in the art will appreciate that by using the instant device, only one size needs to be used. Due to its design, the device can be as small or as large as necessary depending on the size of the iris. Accommodation of the iris by the device can be achieved by inflating the device to any size necessary. Further, due to its ability to be as large as needed, the present device can be used for large animal veterinary medicine for very large eyes. Therefore, while for humans the device has a size range of up to approximately 8-10 mm, for animals, such as, for example, horses, the device can be as big as necessary.

Further, when the exemplary embodiment of the device according to the invention comprising a discontinuous ring or horse-shoe shape is used, its use is the same as the continuous ring except that a window, comprising the discontinuous portion of the ring, is provided allowing the surgeon greater ease of access to the interior of the eye.

Various exemplary embodiments of devices and compounds as generally described above and methods according to this invention will be understood more readily by reference to the following examples, which are provided by way of illustration and are not intended to be limiting of the invention in any fashion.

The following paragraphs enumerated consecutively from one (1) through twenty-three (23) provide for various aspects of the present invention.

1. An iris expansion device comprising:
  an inflatable ring; and
  a groove provided in the outer periphery of the inflatable ring, the groove suitable for engaging the inner periphery of an iris muscle;
  wherein the ring is inflated and the groove engages the iris, increasing the diameter of the pupil.

2. The iris expansion device of paragraph 1, wherein the inflatable ring is discontinuous having a horseshoe shape.

3. The iris expansion device of paragraph 1, further comprising an air-inlet valve.

4. The iris expansion device of paragraph 1, further including one or more positioning loops.

5. The iris expansion device of paragraph 4, wherein one or more of the positioning loops include an eyelet.

6. The iris expansion device of paragraph 1, wherein the groove is approximately 'V; or 'U' shaped.

7. The device of paragraph 1, wherein the device is fabricated from a bio-compatible material.

8. The device of paragraph 7, wherein the bio-compatible material is a rubber, nylon, a plastic, latex, PTFE or combinations thereof.

9. The device of paragraph 8, wherein the device is fabricated from polymers or copolymers of polyamides or polyamides, polyether, polypropylene, polyethylene terephthalate or other phthalate polyesters or copolyesters thereof.

10. The device of paragraph 3, wherein the valve comprises a Luer taper, an osmotic valve, an electromagnetic valve, a check valve, a pinch valve or a thermal expansion valve.

11. The device of paragraph 1, wherein the device fills by elastic recoil or osmotic diffusion.

12. A method of expanding an iris comprising:
  deploying an inflatable ring device in the anterior chamber of an eye;
  inflating the inflatable ring device;
  engaging a groove on the outer periphery of the inflatable ring device with the inner periphery of the iris;
  expanding the inflatable ring device as needed.

13. The method of paragraph 12, wherein the inflatable ring device has an air inlet valve.

14. The method of paragraph 12, wherein the inflatable ring device is discontinuous.

15. The method of paragraph 14, wherein the discontinuous ring has the shape of a horseshoe.

16. The method of paragraph 12, wherein inflating is achieved using a syringe.

17. The method of paragraph 12, wherein inflating is achieved by an osmotic gradient or by elastic recoil.

18. The method of paragraph 12, wherein engaging further comprises positioning the inflatable ring device using a positioning loop attached to the inflatable ring device.

19. The method of paragraph 12, wherein expanding has a range of from about 4 mm to about 10 mm.

20. The method of paragraph 12 further including removing the inflatable ring device.

21. The method of paragraph 20, wherein removing further includes deflating the inflatable ring device.

22. The method of paragraph 20, wherein deflating is performed by removing air through the air inlet valve.

23. The method of paragraph 20, wherein deflating is performed by puncturing the inflatable ring device.

While this invention has been described in conjunction with the various exemplary embodiments outlined above, various alternatives, modifications, variations, improvements and/or substantial equivalents, whether known or that are or may be presently unforeseen, may become apparent to those having at least ordinary skill in the art. Accordingly, the exemplary embodiments according to this invention, as set forth above, are intended to be illustrative, not limiting. Various changes may be made without departing from the spirit and scope of the invention. Therefore, the invention is intended to embrace all known or later-developed alternatives, modifications, variations, improvements and/or substantial equivalents of these exemplary embodiments.

What is claimed is:

1. An iris expansion device comprising:
   an inflatable discontinuous ring comprising two blunt terminal ends that do not interlock together;
   at least three positioning loops located approximately equidistant from each other around the periphery of the inflatable discontinuous ring;
   a U or V shaped groove provided within the outer periphery of the inflatable discontinuous ring; and
   an inlet valve positioned on the inflatable discontinuous ring, wherein the inflatable discontinuous ring comprises a bio-compatible material,
   wherein when the device is inflated, the groove inflates with the ring and the groove of the device is suitable for engaging the inner periphery of an iris muscle,
   wherein when the ring is inflated and the groove engages the iris, the diameter of a pupil is increased, and
   wherein deployment of the discontinuous inflatable ring provides the iris expansion device sized to the individual iris.

2. The iris expansion device of claim 1, wherein the inflatable ring has a horseshoe shape.

3. The iris expansion device of claim 1, wherein one or more of the positioning loops include an eyelet.

4. The iris expansion device of claim 1, wherein the bio-compatible material is a rubber, nylon, a plastic, latex, PTFE or combinations thereof.

5. The iris expansion device of claim 4, wherein the device is fabricated from polymers or copolymers of polyamides, polyether, polypropylene, polyethylene terephthalate or other phthalate polyesters or copolyesters thereof.

6. The iris expansion device of claim 1, wherein the valve comprises a Luer taper, an osmotic valve, an electromagnetic valve, a check valve, a pinch valve or a thermal expansion valve.

7. A method of expanding an iris comprising:
   deploying an inflatable discontinuous ring device as claimed in claim 1 in the anterior chamber of an eye;
   inflating the inflatable ring device;
   engaging the groove within the outer periphery of the inflatable discontinuous ring device with the inner periphery of the iris; and
   expanding the inflatable discontinuous ring device as needed, wherein the groove inflates with the inflatable discontinuous ring device such that when the groove is engaged and inflated with the inner periphery of the iris, the diameter of a pupil is increased.

8. The method of claim 7, wherein the discontinuous ring has the shape of a horseshoe.

9. The method of claim 7, wherein inflating is achieved using a syringe.

10. The method of claim 7, wherein engaging further comprises positioning the inflatable ring device using one of the positioning loops attached to the inflatable ring device.

11. The method of claim 7, wherein expanding has a range of from about 4 mm to about 10 mm.

12. The method of claim 7 further including removing the inflatable ring device.

13. The method of claim 12, wherein removing further includes deflating the inflatable ring device.

14. The method of claim 13, wherein deflating is performed by removing air through the air inlet valve.

15. The method of claim 13, wherein deflating is performed by puncturing the inflatable ring device.

* * * * *